United States Patent [19]

Han

[11] Patent Number: 5,133,701
[45] Date of Patent: Jul. 28, 1992

[54] DISPOSABLE PRESSURE WOUND IRRIGATION DEVICE

[76] Inventor: Sang In Han, 4350 W. Lake, #107-B, Glenview, Ill. 60025

[21] Appl. No.: 596,746

[22] Filed: Oct. 15, 1990

Related U.S. Application Data

[63] Continuation of Ser. No. 334,316, Apr. 6, 1989, abandoned.

[51] Int. Cl.$^5$ .................. A61M 35/00; B67D 5/42
[52] U.S. Cl. .................. 604/289; 128/200.23; 222/389; 222/396; 222/399
[58] Field of Search .............. 604/41, 70, 140-148, 604/278, 289, 290, 293-298, 305, 310, 311; 128/200.14, 200.23, 846, 847; 222/61, 222, 389, 396, 397, 399; 137/505.18, 505.25

[56] References Cited

U.S. PATENT DOCUMENTS

| | | | |
|---|---|---|---|
| 3,178,075 | 4/1965 | Riedl et al. | 222/396 |
| 3,245,591 | 4/1966 | Kneusel et al. | 222/389 |
| 3,314,426 | 4/1967 | Carroll | 128/200.14 |
| 3,561,433 | 2/1971 | Kovach | 604/140 |
| 3,563,423 | 2/1971 | Wilson | 222/396 |
| 3,566,863 | 3/1971 | Law | 604/145 |
| 3,648,696 | 3/1972 | Keith | 128/200.14 |
| 3,752,368 | 8/1973 | Robertson | 222/389 |
| 3,768,475 | 10/1973 | Osborne | 604/140 |
| 3,784,063 | 1/1974 | Otis et al. | 604/141 |
| 3,834,589 | 10/1974 | Morane et al. | 222/396 |
| 3,841,533 | 10/1974 | Carroll et al. | 128/200.23 |
| 4,360,131 | 11/1982 | Reyner | 222/399 |
| 4,456,155 | 6/1984 | Miyata et al. | 222/396 |
| 4,487,334 | 12/1984 | Werding | 222/396 |
| 4,519,528 | 5/1985 | Comment | 222/396 |
| 4,650,094 | 3/1987 | Werding | 222/61 |
| 4,899,914 | 2/1990 | Schweigl et al. | 222/394 |
| 5,059,187 | 10/1991 | Sperry et al. | 604/290 |

FOREIGN PATENT DOCUMENTS

| | | | |
|---|---|---|---|
| 8601463 | 7/1986 | PCT Int'l Appl. | 222/396 |
| 0351214 | 6/1931 | United Kingdom | 604/140 |

OTHER PUBLICATIONS

"Principles Of Emergency Wound Management," Edlich et al., Annals Of Emergency Medicine, Dec. 12, 1988, pp. 1284-1302.

"Cleansing The Traumatic Wound By High Pressure Syringe Irrigation," Stevenson et al., JACEP, Jan. 1976, vol. 5, No. 1, pp. 17-21.

"Effectiveness Of Pulsating Water Jet Lavage In Treatment Of Contaminated Crushed Wounds," Gross et al., The American Journal Of Surgery, Sep. 1972, vol. 124, pp. 373-377.

Sales Brochure, Micro-Aire ® HI Speed Pulse Lavage 4740, Micro-Aire ® Surgical Instruments, Inc. (1986).

Primary Examiner—John D. Yasko
Assistant Examiner—Anthony Gutowski
Attorney, Agent, or Firm—Leydig, Voit & Mayer

[57] ABSTRACT

A disposable pressure wound irrigation device is provided having a reservoir of cleansing solution disposed therein and a pressure chamber for providing a force upon the reservoir such that a liquid stream of cleansing solution is expelled at a constant pressure therefrom. Preferably, the propellant chamber will be provided with a regulator valve fitted within the pressure chamber for constantly monitoring the pressure which urges the chamber against the reservoir. An aimable outlet nozzle is provided through which the cleansing solution is expelled, the nozzle directing the flow of the cleansing solution to the wound surface. A release valve is further provided in order to selectively couple the nozzle with the reservoir, such that the cleansing solution may be evacuated therefrom through a passageway formed by a depression of the valve.

8 Claims, 4 Drawing Sheets

DISPOSABLE PRESSURE WOUND IRRIGATION DEVICE

This is a continuation of Ser. No. 07/334,316, filed on Apr. 6, 1989 (now abandoned).

FIELD OF THE INVENTION

The present invention relates generally to medical devices, and more particularly, to medical devices which are suitable for cleansing traumatic wounds. In its principal aspect, the invention is concerned with improved means for applying cleansing solution to a wound at a constant pressure in order to effectively irrigate the wound surface.

BACKGROUND OF THE INVENTION

It is a commonly known principal of emergency wound management to utilize high pressure irrigation techniques to effectively cleanse traumatic wounds. Typically, both civilian and military physicians utilize high pressure irrigation techniques to eliminate microorganisms and foreign bodies from the wound, thereby preventing infection. As most traumatic injuries occur in highly unsanitary environments, it is not uncommon to find large quantities of foreign bodies present, and even embedded, within the wound.

Experimentation has determined that the effectiveness of wound irrigation, and consequently, of bacteria removal, is directly related to the pressure at which the cleansing solution is delivered to the wound surface. Consequently, physicians have resorted to simple and practical alternatives in order to provide high pressure wound irrigation in the emergency setting. In particular, it has become common practice to utilize a commercially available catheter and syringe to deliver the cleansing solution to the wound area. In practice, a quantity of saline solution is poured into a sterile bowl, allowing the physician to draw a portion of the solution into the syringe. The catheter is then placed in close proximity to the wound surface, the wound being held open by an assistant, and with a pressure applied by the physician to the saline plunger, the saline solution is expelled into the wound area. However, as pressure at which the fluid irrigates the wound is dependent upon the rate at which the syringe plunger is depressed, and thus dependent upon the pressure applied by the physician over the rather long stroke of a conventional syringe, it is quite difficult to maintain a constant, or in some cases, an adequately high pressure at the irrigant/wound interface. Furthermore, since the cleansing process requires a substantial quantity of irrigant fluid to be passed through the wound, the syringe must continually be refilled. However, in order to avoid contaminating the cleansing solution with bacteria from the wound, the catheter must be removed each and every time the irrigant is drawn from the sterile bowl, then replaced prior to its use.

In order to avoid this time consuming and burdensome task, syringes have been developed having one-way valves attached to the syringe barrel for connection with a cleansing solution source. Typically, the saline solution source is an IV bag which must be hung, the solution being delivered to the syringe through standard IV plastic tubing. After evacuating the syringe chamber, the physician need only return the syringe plunger to its full position, thereby drawing additional saline solution into the syringe chamber. However, while the catheter need not be changed during the irrigation process, the IV bag and tube can be cumbersome, and the process remains a two person operation. Furthermore, since the physician is required to exert manual force on the syringe plunger to irrigate the wound, the ability to achieve constant and adequate pressure is no better than with use of a simple syringe as described above.

Consequently, attempts have been made to develop high pressure irrigation devices and effective wound irrigators for hospital use. However, these devices have suffered from significant disadvantages in that they are expensive and cumbersome, and are difficult to sterilize, raising the possibility of delivering contaminated cleansing solution to the wound surface. As a result, these devices have seen limited use in the hospital setting.

SUMMARY OF THE INVENTION

Accordingly, it is a primary object of the invention to provide a disposable wound irrigation device which provides a constant, high pressure fluid stream at the wound surface.

It is a further object of the present invention to provide a disposable wound irrigation device which allows the physician to perform the irrigation procedure without assistance.

Furthermore, it is an object of the present invention to provide a disposable wound irrigation device having a self-contained, cleansing solution source.

Yet another object of the invention to provide a wound irrigation device which is disposable and economical.

In general, the present invention contemplates a disposable self-contained wound irrigator containing a propellant and a cleansing solution supply in which the propellant is used to controllably expel the cleansing solution through an aimable outlet at substantially constant pressure.

A housing is provided having a reservoir formed therein for containing a quantity of cleansing solution. Force applying means for providing an evacuating force to evacuate the reservoir are positioned adjacent thereto. An aimable outlet is provided through which a liquid stream of cleansing solution can be expelled and directed to a wound surface. Control means for selectively coupling the reservoir with the aimable outlet are included for controllably releasing the cleansing solution. Means for regulating the pressure within the reservoir are provided such that the cleansing solution is expelled through the aimable outlet at a substantially constant pressure.

According to a feature of the invention, a chamber containing a compressed gas is provided beneath the reservoir within the irrigator housing such that upon release of the compressed gas, an evacuation force is imposed on the cleansing solution. Upon opening a valve to connect the reservoir with the aimable outlet, the cleansing solution is expelled therethrough at a substantially constant pressure.

According to a preferred embodiment of the present invention, a regulator valve is fitted within the chamber for controllably releasing the compressed gas between the housing and the bottom of the chamber, thereby forcing the housing against the cleansing solution in the reservoir at a predetermined pressure determined by the regulator valve.

BRIEF DESCRIPTION OF THE DRAWINGS

For the purpose of facilitating and understanding the invention, the accompanying drawings illustrate a preferred embodiment. The above and other objects of the invention, as well as the features thereof is summarized above will become more apparent from the following description when taken in conjunction with the accompanying drawings.

DESCRIPTION OF THE PREFERRED EMBODIMENT

Figure 1:
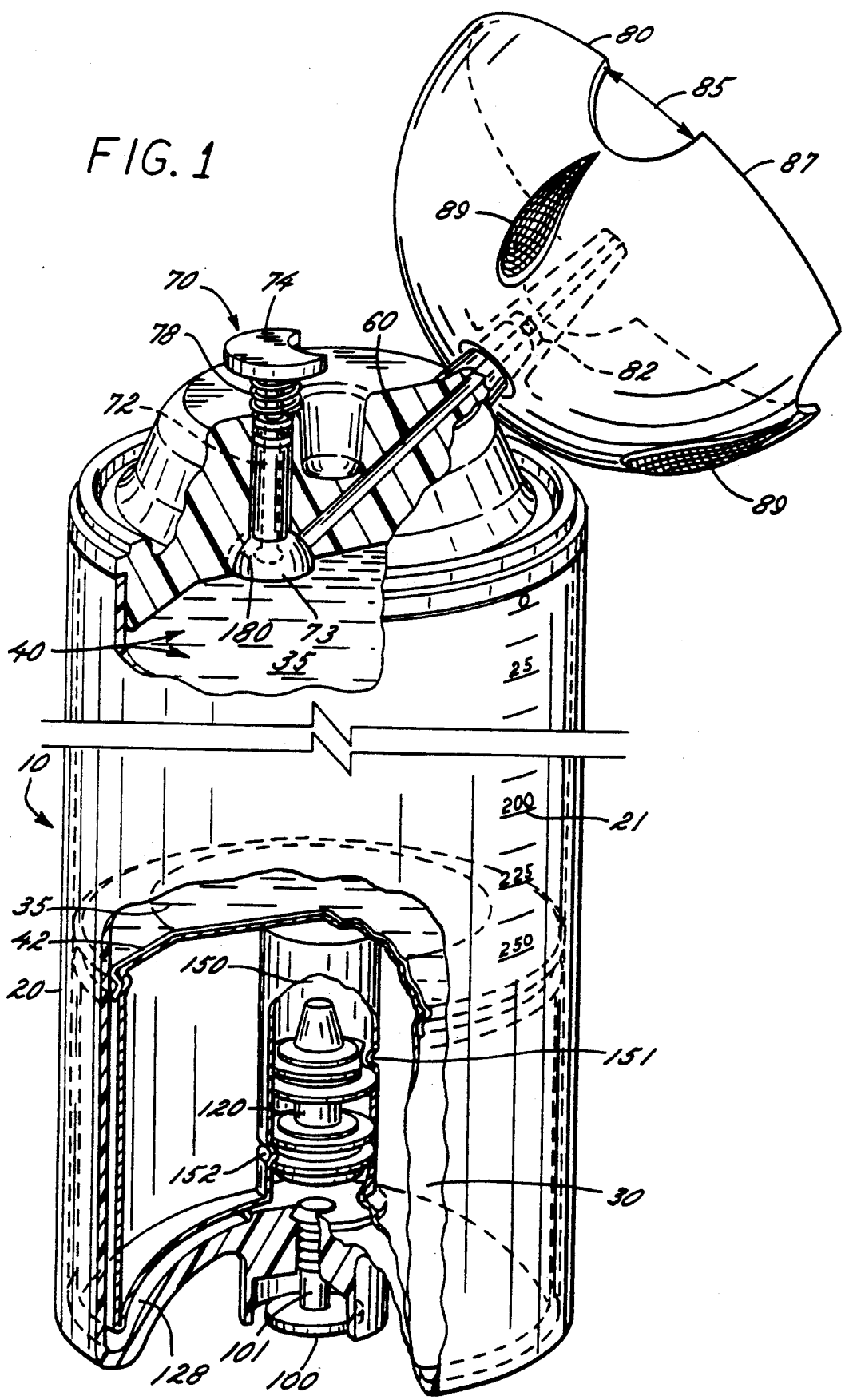
FIG. 1 is a perspective view of a disposable wound irrigation device in accordance with the present invention having portions broken away to show the internal structure thereof.

While the invention is susceptible of various modifications and alternative constructions, a certain illustrated embodiment thereof has been shown in the drawings and will be described below in detail. It should be understood, however, that there is no intention to limit the invention to the specific form disclosed, but on the contrary, the intention is to cover all modifications, alternative constructions and equivalents falling within the spirit and scope of the invention as defined by the appended claims.

Figure 2:
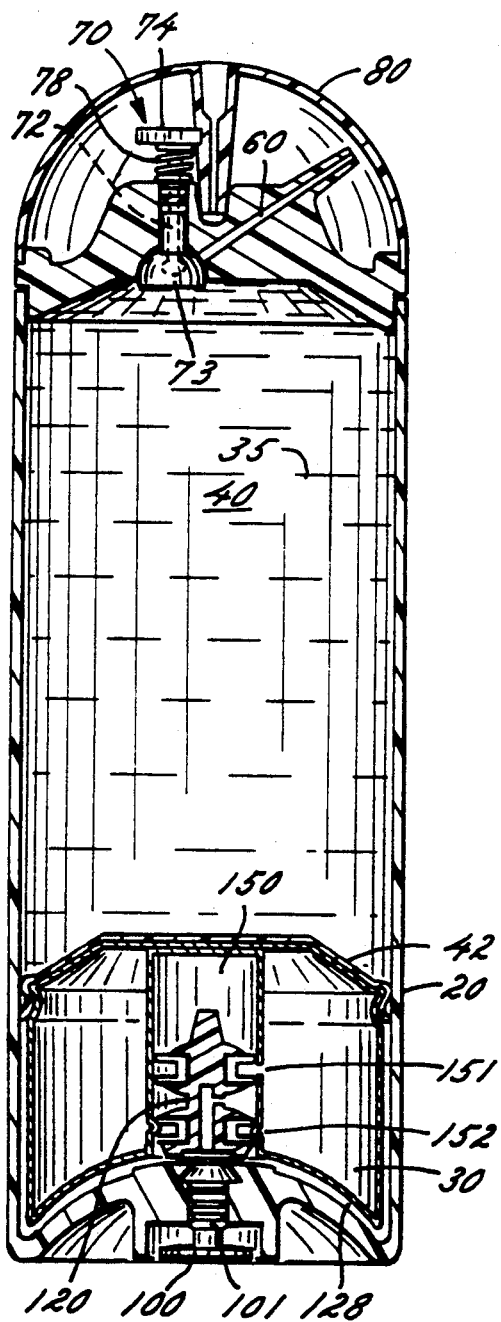
FIG. 2 is a sectional view of a disposable wound irrigation device.

Turning now to the drawings, and first to FIG. 1, there is shown a disposable wound irrigator 10 embodying the present invention. Disposed within container 20 are force applying means 30 and reservoir 40 which contains a cleansing solution 35 to be passed through the wound area. Mounted in an upper end of the irrigation assembly 10 are aimable outlet means 60 and control means 70, both of which interact to allow for the release of the cleansing solution 35 from within the reservoir 40. As best shown in FIG. 2, removable cap enclosure 80 is attached to the upper end of container 10, thereby enclosing control means 70 and aimable outlet means 60 in a substantially sanitary environment. As disclosed, the removable cap enclosure 80 is adaptable to be attached to the aimable outlet means 60 when inverted such that an effective guard is created in order to prevent backsplash of the cleansing solution upon contact with the wound area.

In order to activate the irrigator assembly 10, actuation means 100 is depressed so as to contact and displace regulating valve 120. The regulating valve 120 acts as a means for indirectly regulating the pressure within the reservoir 40, thus creating a constant fluid pressure at the wound surface when fluid is released. Upon displacement of the valve 120, a compressed gas escapes from within the force applying means 30, thereby providing a pressure increase in the cavity 128 between the bottom of the container 10 and the force applying means 30, such pressure increase urging the force applying means 30 and movable sealing surface 42, attached thereto, upward. The physician may then depress the control means 70, thereby creating a passageway 181 between the reservoir 40 and aimable outlet means 60 through which the cleansing solution 35 may be forced as the force applying means 30 and movable sealing surface 42 move upwardly.

Figure 3:
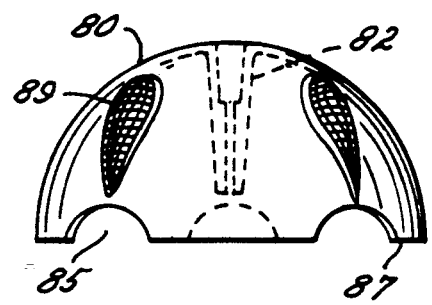
FIG. 3 is a fragmentary and perspective view of the hemispherical enclosure of the present invention.

In keeping with the disposability feature of the invention, it should be appreciated that many components of the irrigation assembly can be constructed of inexpensive, polymeric material, and manufactured through commonly known injection molding techniques. In this preferred embodiment, it should be appreciated that the container will be constructed of a transparent plastic material such that the amount of cleansing solution 35 present within the reservoir 40 may be monitored. Furthermore, it should be appreciated that a number of packaging techniques can be utilized in order to provide the physician with a sterile irrigation assembly. For example, the entire device may be packaged within a sterile, puncture-resistant bag, such bag to be opened by the medical personnel at the time of use. It is further possible to seal only the enclosure removable cap in a sterile fashion in order to prevent entrance of foreign articles or bacteria through the semicircular holes or nozzle opening as shown in FIG. 3. These packaging methods ensure that the inner surface of the cap 80 will remain sanitary, an important consideration as this surface acts as the primary contact area between the irrigation assembly and the wound area.

As shown in FIG. 3, the removable cap enclosure 80 is hemispherically shaped having an inwardly extending catheter opening 82 such that the cap is inverted and attached to the aimable outlet means 60. Consequently, the cap 80 serves not only to provide a sterile enclosure for the control means 70 and aimable outlet means 60, but further provides a guard against backsplash of the cleansing solution 35. Since the cleansing solution 35 is expelled under pressure, substantial backsplash is likely to occur when the solution contacts the wound surface, thus subjecting the physician to unwanted contaminant contact. Accordingly, with the cap 80 invertedly mounted on aimable outlet means 60, the physician is effectively shielded from contaminant contact as the contaminated solution is deflected from the wound surface. In this preferred embodiment, the cap 80 is constructed of a clear plastic material allowing the physician to view the wound during the irrigation process. The hemispherical cap 80 has further been provided with semicircular openings 85, distally spaced about the perimeter of the cap edge 87. In the event that the device must be placed into direct contact with the wound surface, the semicircular openings 85 will serve to drain the contaminated fluid from the wound area as the irrigation process is performed. Furthermore, the cap 80 has been provided with extending finger grips 89 to provide an improved gripping surface for the physician as the cap 80 is disconnected from the end of container 20.

In order to provide an exit through which the cleansing solution can be expelled, aimable outlet means 60 is provided in an upper surface of the container 20. In keeping with the invention, it is highly desirable to have an exit fluid pressure of 7-8 PSI, a pressure which has been deemed to be effective in wound irrigation techniques. In this preferred embodiment, in order to provide an opening which will allow sufficient flow of the cleansing solution 35 to the wound surface, while providing an exit pressure of 7-8 PSI, a nozzle 82, having a cup opening substantially equivalent to the port of a standard 19 gauge hypodermic needle, is utilized as the aimable outlet means. It will be appreciated that various instruments can be incorporated herein to provide an aimable outlet means with similar operational characteristics.

Cooperating with nozzle 60, and located proximate thereto, is control means 70. In this preferred embodiment, the control means 70 is a release valve extending through the upper surface of the container 20 into an valve seat 180 within the reservoir 40. Upon manual depression of the valve 70, a passageway 181 is created through which the cleansing solution is communicated with the nozzle 60, and upon activation of the irrigator, forced therethrough. In keeping with the invention, the stroke length through which the valve 70 must be depressed is considerably less than the distance through which a syringe plunger must be displaced in a typical irrigation procedure. Furthermore, the valve 70 is easily depressed by the finger pressure of a physician and the pressure at which the fluid is expelled is completely unrelated to the depression force applied to the valve 70.

As shown in this preferred embodiment, depressible valve 70 is constructed in a two piece format. The stem section 72, extends through the upper surface of the container 20 for connection with the resilient gasket member 73, the gasket 73 preventing leakage of the cleaning solution 35 around the valve stem 72 when the valve 70 is depressed. Push button surface 74, has been provided as a surface upon which a depression force may be applied by a physician's finger. As further disclosed, the release valve 70 is fitted with a compression spring 78 such that the valve 70 is automatically urged into valve seat 180, thereby sealing the passageway 181 when a depression force is not exerted.

As further shown in the drawings, the reservoir 40 is filed with a cleansing solution 35, the reservoir occupying a substantial portion of the interior volume of the irrigator assembly 10. Standard wound irrigation techniques require the use of approximately 250 milliliters of cleansing solution in order to effectively clean a typical traumatic wound. Accordingly, in this preferred embodiment, the reservoir is capable of containing an equivalent volume of cleansing solution, however, it will be appreciated that the reservoir volume is only a design dimension which is not herein limited. As disclosed in FIG. 1, the transparent container 20 has been provided with calibrated markings 21 to further facilitate accurate monitoring of the quantity of cleansing solution 35 remaining within the reservoir 40. Preferably, the cleansing solution contained within the reservoir will be a saline solution, but it will be appreciated that a number of alternative irrigants are available and adaptable for use in the present invention.

Reservoir 40 is provided with a movable, sealing surface 42, mounted upon an upper surface of the force applying means 30. In particular, the surface 42 serves to prevent leakage of the cleansing solution 35 into the area occupied by the force applying means 30, and further serves as the surface upon which the evacuation force is distributed. Accordingly, upon activation of the force applying means 30, and a corresponding depression of valve 70, the movable sealing surface 42 and force applying means 30 are propelled, as an integral unit, through the reservoir 40, urging the cleansing solution 35 through the nozzle 60. It will be further appreciated that the movable surface 42 will be constructed of a resilient material which is non-corrosive when introduced to the cleansing solution 35 and provides an effective seal at the container wall.

Figure 7:
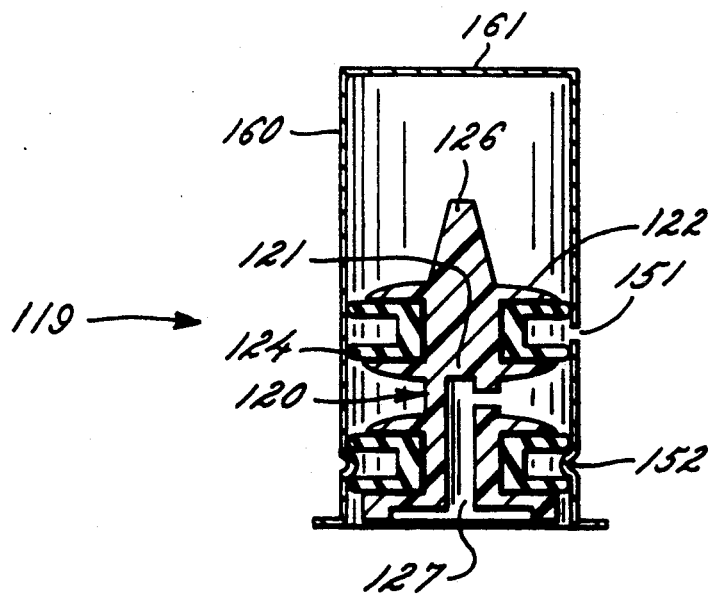
FIG. 7 is an enlarged sectional view of an exemplary valve of the present invention shown in its closed position.

In furtherance of the present invention, force applying means 30 is disposed within the container 20 in an area adjacent the reservoir 40. As disclosed herein, the propellant means, 30 is a cylindrical chamber in which a compressed gas, such as air, is confined. It should be appreciated that this chamber can be constructed of a material which is light weight, yet of sufficient strength so as to contain a pressurized gas. Such material qualities are typically found in metals such as aluminum, but can further be created through the use of high strength composite resins. Mounted within the chamber 30 is a regulator valve, generally illustrated at 119. Valve 119 includes a valve member 120 mounted for reciprocation in cylindrical duct 150. In order to secure the valve member 120 in its closed position, as shown in FIG. 7, extending ridge 152 has been provided. Furthermore, an exit aperture 151 is formed in the cylindrical duct peripheral wall 160, thereby providing an exit through which the compressed gas flows from within the chamber 30.

Figures 5, 6:
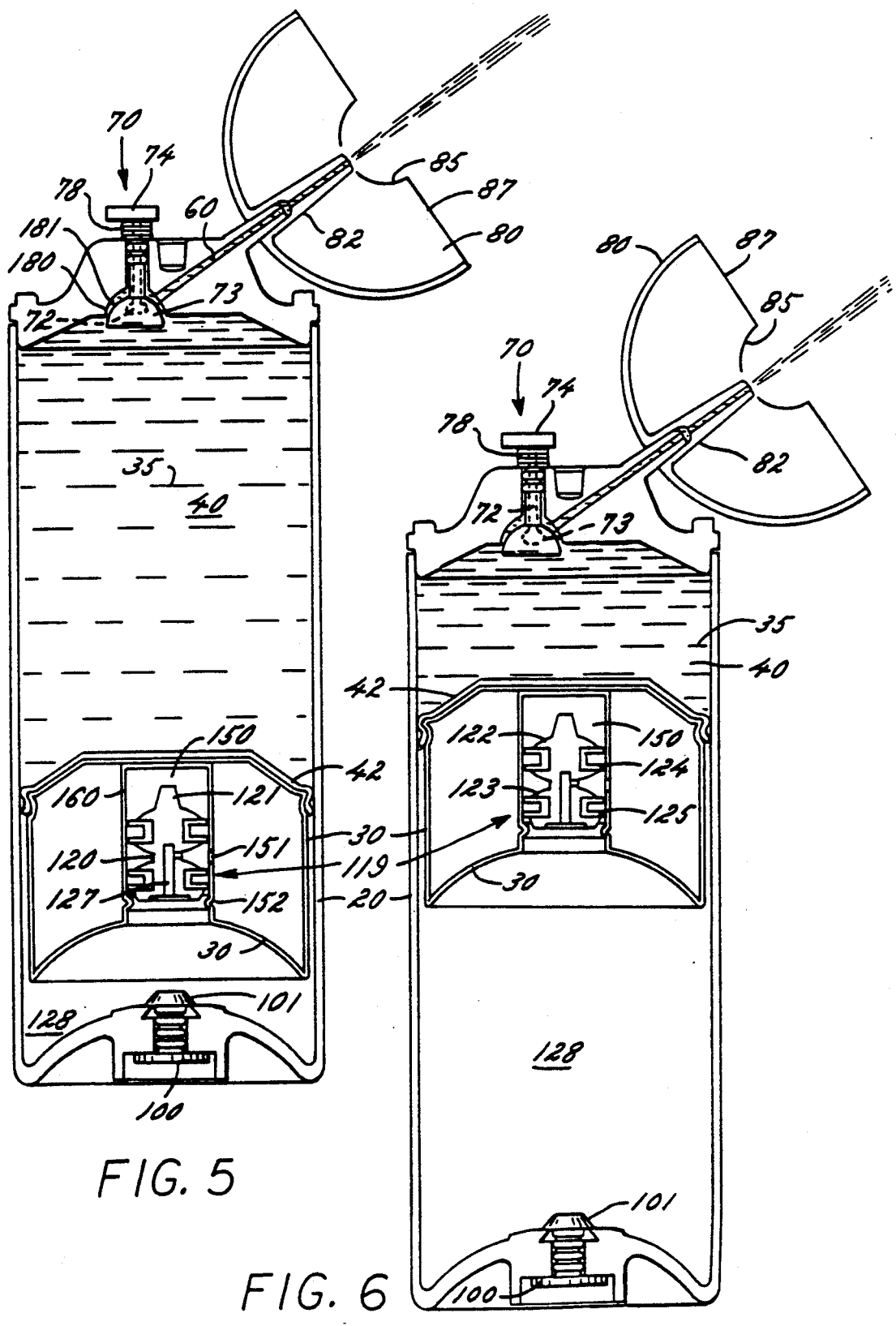
FIG. 5 is a sectional view of a disposable wound irrigation device in its operational state.
FIG. 6 is a sectional view of the disposable wound irrigation device of FIG. 5 wherein an additional volume of irrigant has been expelled.

As best shown in FIGS. 5 and 6, upon opening regulator valve 120 by depressing actuation means 100, the compressed gas escapes through exit aperture 151 into cavity 128 formed between an end surface of the housing container 20 and the bottom of regulator valve 119. As this compressed gas expands, the pressure in cavity 128 increases, thereby forcing the chamber 30 and the movable surface 42 against the cleansing solution 35, imposing a force thereupon. Accordingly, upon depression of valve 70, the cleansing solution 35 is forced through nozzle 60, and expelled against the wound surface. As shown FIG. 6, for so long as a depression force is maintained on release valve 70, the pressure created in cavity 128 will continue to force the cleansing solution 35 from within the reservoir 40 until the irrigator is emptied.

In accordance with the invention, the disposable irrigator is provided with means for regulating the pressure applied to the cleansing solution 35, such that a substantially constant pressure is maintained as the solution 35 strikes the wound surface. In the illustrated embodiment, such means are generally shown as regulator valve 119, having a valve member 120 mounted for reciprocation within cylindrical duct 150. As previously discussed, it is highly desirable to maintain a pressure of 7-8 PSI at the interface of the wound surface.

Figure 8:
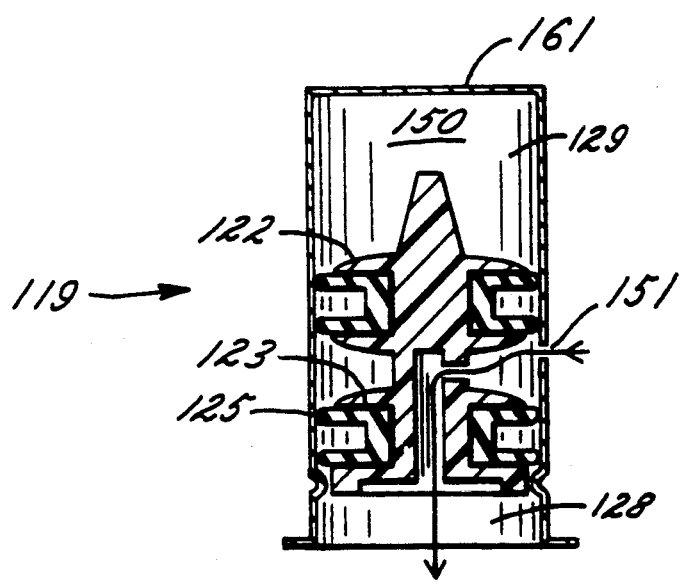
FIG. 8 is an enlarged sectional view of the valve of FIG. 7 shown in its open position.
Figure 9:
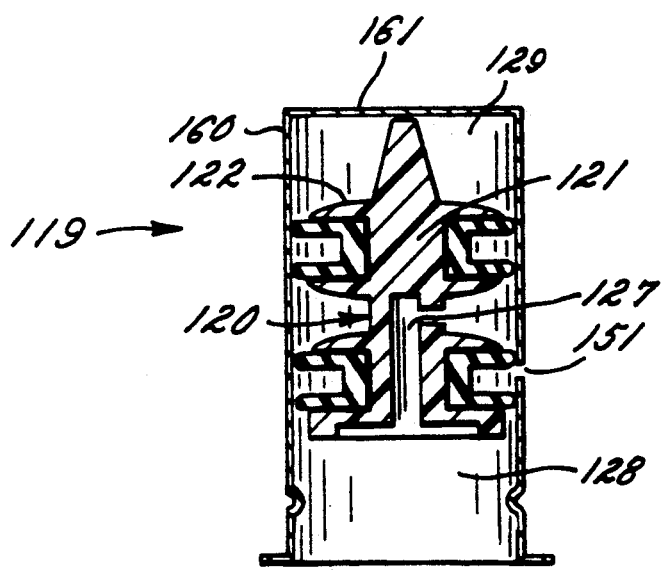
FIG. 9 is an enlarged sectional view of the valve of FIG. 7 shown in a regulated closed position.

FIGS. 7, 8 and 9 illustrate the operational characteristics of regulator valve 119, such valve serving to ensure that a constant pressure is provided as the cleansing solution 35 is directed against the wound surface. Valve member 120 includes a pair of wall engaging valve seats 122, 123 joined at 121 to form a unitary valve member 120. These valve seats 122, 123 are formed by two spaced apart circular gasket retainers which extend radially outward from the axis of the valve member 120. Mounted between the distally spaced retainers are ring gaskets 124, 125, such gaskets providing a seal between the valve seats 122, 123 and the peripheral wall 160, and, when positioned over the exit aperture 151, the gaskets 124, 125 further serve as sealing valves. As shown in FIG. 7, the upper valve 124 is positioned over exit aperture 151, which is thereby secured in its closed position by extending ridge 152, thereby preventing flow of the compressed gas from within the chamber 30.

Figure 4:
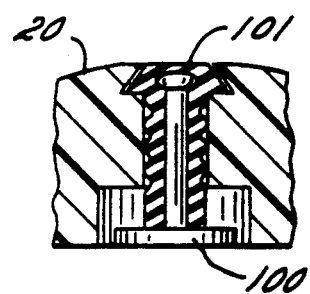
FIG. 4 is an enlarged sectional view of the actuating member as shown in FIG. 2.

Upon depression of actuation means 100 (FIG. 1), the valve member 120 is displaced into its open position, as shown in FIG. 8, thereby allowing the compressed gas to escape through exit aperture 151 into gas channel 127, the gas following along the path described by the arrow in FIG. 8. Actuation means 100 has been provided with sealing gasket 101 (FIG. 4) in order to prevent the escape of compressed gas therethrough as the pressure in cavity 128 increases. As the compressed gas expands and increases the pressure within cavity 128, the chamber 30 and surface 42 are forced against the reservoir 40, thereby imparting a force throughout the cleansing solution 35. When the pressure in space 128 increases to a level greater than the pressure within space 129, the valve member 120 is displaced upwardly within the cylindrical duct 150. The valve 120 will continue to rise within the cylindrical duct 150 until the pressure within space 129 becomes elevated to a predetermined amount. In accordance with this preferred embodiment, it has been determined that a pressure of 21 PSI in cavity 128, and accordingly, 21 PSI within the reservoir 40, will result in a liquid stream pressure of 7-8 PSI at the wound surface. Accordingly, when a pressure of 21 PSI has been attained, the lower valve 125 will simultaneously be displaced over the exit aperture 151, as shown in FIG. 9, thereby preventing any further pressure elevation within cavity 128. Consequently, under the conditions shown in FIG. 9, it should be understood that both the pressure in space 129 and that in cavity 128, are about 21 PSI.

Upon further evacuation of the cleansing solution 35, the chamber 30 and surface 42 will continue to rise, as shown in FIG. 6, thereby increasing the volume of cavity 128, resulting in a decrease of the pressure therein. Accordingly, since the pressure in space 129 remains at 21 PSI, a value greater than the resultant pressure in cavity 128, the regulator valve 120 will be urged downward into the position shown in FIG. 8, allowing for the release of additional compressed gas into the opening 128. Consequently, the pressure in cavity 128 will again be increased to a level of 21 PSI, thereby causing the valve 120 to again rise to its regulated position as shown in FIG. 9. Through the implementation of the slidable regulator valve 119, as disclosed in this preferred embodiment, the pressure at which the cleansing solution 35 is evacuated from the irrigation assembly 10 is continually monitored and maintained constant at a predetermined level.

It should be appreciated that the predetermined pressure at which the fluid is constantly expelled from the irrigation assembly is a function of the volumetric dimensions of the cylindrical duct 150 and the valve member 120. In this preferred embodiment, the volume of the valve member 120 is increased by the addition of a frusto-conical section 126 disposed upon the upper valve seat 122. Frustoconical section 126 serves as a safety device in the event that the pressure within cavity 128 increases rapidly. Should such circumstances occur, section 126 will contact the end wall 161 of the valve 119, thereby ensuring that the exit aperture 151 is sealed by lower valve seat 123 and gasket 125, preventing unregulated release of the compressed gas contained within chamber 30.

The volumetric dimensions have been calculated such that when the valve 120 has compressed the gas in space 129 to a predetermined pressure, 21 PSI in this preferred embodiment, the valve 125 will be placed over the exit aperture 151, as best seen in FIG. 9. Accordingly, using alternate design dimensions, it should be appreciated that the pressure at which the cleansing solution 35 is expelled from the irrigation assembly 10 may be either higher or lower than 7-8 PSI.

In an exemplary embodiment of the present invention, the volumetric dimensions of the valve member 120 and the cylindrical duct 150 have been calculated in order to provide a predetermined pressure within space 129 of 21 PSI.

The volumetric considerations of primary significance concern the volume of space 129, the volume above the member 120. Physical principles commonly known in the art dictate that the mathematical product of the initial pressure and volume ($P_1V_1$) is equivalent to the mathematical product of the final pressure and volume product ($P_2V_2$). The initial volume of the space 129 in the preferred embodiment is equal to the volume of the cylindrical space above upper valve seat 122, subtracting the volume of frusto-conical section 126. According to a preferred embodiment of the present invention, the frusto-conical section occupies a volume equivalent to a 1 mm height of the space 129, and, the space above aperture 151 is 18 mm in height. Accordingly, incorporating a radius dimension of 8 mm, the volume is thus, 18-1 multiplied by the cross-sectional area of the cylindrical duct, the calculation yielding a volume ($V_1$) equivalent to the number $17 \times (0.8 \times 0.8 \times \pi)$.

When the valve member 120 has been displaced to its regulated position, as shown in FIG. 9, the corresponding volume within space 129 is decreased, thereby increasing the pressure therein. In this preferred embodiment, the valve member 120 is displaced through a 10 mm stroke when moving from the position of FIG. 7 to the position of FIG. 9, thereby decreasing the height of the space 129 by a corresponding amount. Accordingly, the resultant volume ($V_2$) of space 129 is $7 \times (0.8 \times 0.8 \times \pi)$. Accordingly, inserting the calculated volumes within the aforementioned physical equation, $P_1V_1=P_2V_2$, the corresponding pressure in space 129 can be calculated from the mathematical equation $P_2=P_1V_1/V_2$. Utilizing a standard atmospheric pressure, 14.7 PSI, as the initial pressure ($P_1$) within space 129, as shown in FIG. 7, the calculation yields an elevated pressure of 21 PSI within the spaced 129 when the valve member 120 is displaced into its regulated position as shown in FIG. 9. Accordingly, the corresponding pressure in cavity 128 will be 21 PSI, thereby imposing an equivalent pressure upon cleansing solution 35, causing the solution to be expelled through opening 82 and contact the wound surface a substantially constant pressure of 7-8 PSI. It should be understood that utilizing these physical principles, one can determine the pressure at which the irrigator will be regulated, and consequently, can determine the pressure at which the cleansing solution 35 will strike the wound surface.

I claim as my invention:

1. A unitary, hand-held disposable pressure wound irrigator comprising:
   a substantially sealed non-refillable housing containing a quantity of sterile cleansing solution;
   means in the housing for controllably releasing said solution from said housing;

an aimable outlet affixed to the housing for directing a stream of sterile cleansing fluid from the housing into a bodily wound for controllable cleansing thereof; and pressure means within the housing providing a force for evacuating said solution from said housing, said pressure means including a cylindrical container slidably fit within said housing adjacent said solution and opposite said releasing means, a source of compressed gas within said cylindrical container, and a regulating valve for controllably releasing said compressed gas into a cavity formed between said cylindrical container and a bottom of said housing thereby to force said cylindrical container against said cleansing solution at a predetermined pressure determined by said regulator valve, said pressure means maintaining substantially constant pressure sufficient to dislodge debris from the wound independent of the level of cleansing solution.

2. A disposable hand-held, and unitary pressure wound irrigator comprising:
   a housing of a size and shape adapted to be hand-held and readily manually manipulatable;
   a substantially sealed non-refillable reservoir formed within said housing;
   a cleansing solution contained within said reservoir;
   force applying means contained in the housing and including a source of propellant, separating means associated with the force applying means for separating the cleansing solution form the propellant while applying an evacuating force to evacuate the cleansing solution from said reservoir;
   aimable outlet means on the housing so constructed and arranged as to be directed toward a bodily wound by manual manipulation of the housing, the outlet having an exit opening for directing a liquid steam of said cleansing solution into a wound as directed by manipulation of the housing;
   valve means for regulating the pressure applied by the force applying means to the cleansing solution in the reservoir such that substantially all of said cleansing solution is expelled through said aimable outlet means into the wound at a substantially constant pressure and at a sufficient pressure to dislodge debris from the wound;
   hand-operable control means on the container and positioned for operation by a hand holding the housing and aiming the outlet for selectively coupling said reservoir with said aimable outlet means for controllably releasing said cleansing solution therethrough into the wound;
   the valve means for regulating the pressure is a regulator valve for controllably releasing the source of propellant, and the valve means for regulating further comprising:
   a cylindrical duct closed at one end and having a peripheral wall;
   a plurality of wall engaging valve seats; and
   a connecting member coupling said plurality of wall engaging valve seats, said connecting member further including a gas channel through which the propellant flows when the valve is opened.

3. A disposable pressure wound irrigator as claimed in claim 2 wherein each of said plurality wall engaging valve seats includes two gasket retainers extending radially outward from the axis of said cylindrical duct, and gaskets in the gasket retainers engaging said duct peripheral wall, said gasket retainers being distally spaced so as to define a seat for a valve gasket.

4. A disposable pressure wound irrigation assembly as claimed in claim 3 wherein two valve seats are disposed equidistant from an opening in said connecting member, said opening defining an outlet of said gas channel.

5. A disposable pressure wound irrigation assembly as claimed in claim 2 wherein said gas channel extends through a bottom surface of said regulator valve into an opening between an end surface of said housing and said regulator valve.

6. A disposable pressure wound irrigation assembly as claimed in claim 2 wherein said cylindrical duct further includes a retaining ridge extending transversely from said peripheral wall for retaining said regulator valve in a closed position.

7. A disposable pressure wound irrigation assembly as claimed in claim 2 wherein said cylindrical duct further includes an exit aperture in said peripheral wall through which said propellant flows.

8. A disposable, hand-held and unitary pressure wound irrigator comprising, in combination, a cylindrical container having a substantially sealed non-refillable reservoir formed in a portion thereof, the container being of a size and shape adapted to be hand-held, a volume of a line cleansing solution in the reservoir, a nozzle projecting from the reservoir to the exterior of the container and oriented with respect to the container for ready direction into or toward a wound by manual manipulation of the hand-held container, the nozzle having a discharge orifice for ejecting a fluid stream of saline solution into a wound for cleansing thereof, a manually operable release valve on the container positioned for finger actuation, the release valve being so constructed and arranged as to couple the reservoir to the nozzle for controllably releasing the saline solution through the nozzle, and force applying means in the container including a source of propellant, separating means associated with the force applying means for separating the cleansing solution from the propellant while applying a substantially constant orientation and fill level independent pressure to the solution in the reservoir so that activation of the release means will cause the release of a directed stream of the saline solution through the nozzle at a substantially constant pressure, the container, nozzle and release valve being arranged with respect to each other and the container such that the irrigator can be held, and triggered with a single hand while aiming the nozzle in any necessary orientation to irrigate a bodily wound; and
   the force applying means further comprising a cylindrical housing slidably fit within the cylindrical container adjacent the reservoir and opposite the release valve, a source of compressed gas within the cylindrical housing, and a regulating valve for controllably releasing the compressed gas from the housing into a cavity formed between the cylindrical housing and a bottom of the cylindrical container, thereby to force the cylindrical housing against the saline solution in the reservoir at a predetermined pressure determined by the regulator valve.

* * * * *